United States Patent
Halpern Chirch et al.

(10) Patent No.: US 10,231,919 B2
(45) Date of Patent: *Mar. 19, 2019

(54) EXCELLENT WATER RESISTANCE WITH AN ASSOCIATION OF TWO FILM FORMERS

(71) Applicant: L'OREAL, Paris (FR)

(72) Inventors: Susan Halpern Chirch, Basking Ridge, NJ (US); Anil Shah, East Windsor, NJ (US); Anne-Laure Suzanne Bernard, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/337,958

(22) Filed: Oct. 28, 2016

(65) Prior Publication Data

US 2018/0116944 A1    May 3, 2018

(51) Int. Cl.
| | |
|---|---|
| *A61K 8/85* | (2006.01) |
| *A61K 8/81* | (2006.01) |
| *A61Q 1/00* | (2006.01) |
| *A61Q 17/04* | (2006.01) |
| *A61Q 1/02* | (2006.01) |

(52) U.S. Cl.
CPC .............. *A61K 8/85* (2013.01); *A61K 8/8152* (2013.01); *A61Q 1/02* (2013.01); *A61Q 17/04* (2013.01); *A61K 2800/594* (2013.01)

(58) Field of Classification Search
CPC .. A61K 8/85; A61K 8/8152; A61K 2800/594; A61Q 1/02; A61Q 17/04
See application file for complete search history.

(56) References Cited

U.S. PATENT DOCUMENTS

| | | | |
|---|---|---|---|
| 8,557,227 B2 | 10/2013 | Simonnet | |
| 8,691,192 B1 | 4/2014 | Halpern | |
| 2007/0246058 A1* | 10/2007 | Bodelin | A45D 40/265 132/218 |
| 2007/0264216 A1 | 11/2007 | McEntire | |
| 2008/0268002 A1* | 10/2008 | Dumousseaux | A61K 8/0241 424/401 |
| 2014/0242135 A1* | 8/2014 | Zwiebel | A01N 43/653 424/403 |

OTHER PUBLICATIONS

Interpolymer, Syntran® 5760, 2016.*
Eastman, Eastman AQTM 55S Polymer, 2016.*

* cited by examiner

*Primary Examiner* — Sreenivasan Padmanabhan
*Assistant Examiner* — Genevieve S Alley

(57) ABSTRACT

The present disclosure relates to a cosmetic composition comprising: (a) Sulfopolyester; and (b) Styrene/Acrylates/Ammonium Methacrylate copolymer; wherein the combination of the sulfopolyeseter and Styrene/Acrylates/Ammonium Methacrylate copolymer improves the water resistance of the cosmetic composition and reduces the stickiness of the cosmetic composition.

14 Claims, No Drawings

EXCELLENT WATER RESISTANCE WITH AN ASSOCIATION OF TWO FILM FORMERS

FIELD OF THE DISCLOSURE

The present disclosure is directed to cosmetic compositions. The compositions are useful in cosmetic, skin care and sun care. More specifically, the compositions contain the combination of Sulfopolyester and Styrene/Acrylates/Ammonium Methacrylate copolymer.

BACKGROUND

The need for compositions for imparting water resistance and aiding retention of active ingredients in personal care compositions is well known. Without them, personal care actives may wash off, wear off, be re-emulsified, or otherwise lose their efficacy. The problem with current water resistance imparting polymers is they are typically very tacky and impart bad aesthetic feel to consumers when formulated into leave-on formulations. For reference, aesthetics is one of the most important considerations in a consumer's selection of, or at least loyalty to, a personal care composition. Accordingly, what is needed is a water resistance polymer which possesses improved aesthetic performance, as well as excellent retention of active ingredients when water is present. The inventors of the instant disclosure discovered a novel way to boost water resistance by combining Sulfopolyester and Styrene/Acrylates/Ammonium Methacrylate copolymer.

SUMMARY OF THE DISCLOSURE

The composition of the instant disclosure typically contains: (a) Sulfopolyester; (b) Styrene/Acrylates/Ammonium Methacrylate copolymer; wherein the combination of Sulfopolyester and Styrene/Acrylates/Ammonium Methacrylate copolymer improves the water resistance of the cosmetic sunscreen composition and reduces the stickiness of the cosmetic sunscreen composition.

The instant disclosure relates to cosmetic compositions and methods that are unique in their ability to protect the skin. The inventors surprisingly discovered that when certain film formers are combined in a particular ratio, they show an exceptional Water Resistance. The combination also improves the texture of the compositions.

DETAILED DESCRIPTION OF THE DISCLOSURE

The instant disclosure relates to a cosmetic composition comprising: (a) Sulfopolyester; (b) Styrene/Acrylates/Ammonium Methacrylate copolymer; wherein the combination of Sulfopolyester and Styrene/Acrylates/Ammonium Methacrylate copolymer improves the water resistance of the cosmetic composition, and reduces the stickiness of the cosmetic composition.

The cosmetic compositions described herein may contain at least one sulfopolyester polymer. Sulfopolyester polymers are generally referred to polyesters containing ionic sulfonate (SO3-) groups, particularly to those synthesized using a sulfomonomer such as, for example, 5-sodiosulfoisophthalic acid (5-SSIPA or SIP) or dimethyl 5-sodiosulfoisophthalate, as one of the diacids in the polyester compositions. Such sulfopolyester polymers are well known to those skills in the art and are commercially available from Eastman Chemical Company under the Eastman AQ™ family of polymers. The polymers are linear, amorphous polyesters that can be dispersed in water without the assistance of surfactants or amines. This water dispersibility is attributed to the ionic nature of the sulfonate substituents attached to the polymer chains. In one embodiment, Polyester-5 is a suitable sulfopolyester polymer for use in this invention and is known as Eastman™ AQ 38S Polymer.

As mentioned above, the Polyester-5 may be in an amount of about 0.5 to about 4 wt. % based on the total weight of the cosmetic composition. In some instance, the amount of Polyester-5 is, however, from about 1 to about 4 wt. %, about 1.5 to 4 wt. %, about 2 to about 4 wt. %, about 1 to about 3.5 wt. %, about 1 to about 3 wt. %, or about 2 to about 3 wt. %.

The cosmetic compositions described herein also contain Styrene/Acrylates/Ammonium Methacrylate copolymer which is a suitable acrylate copolymer for use in this invention and is known as Syntran® latex 5620 CG.

As mentioned above, the Styrene/Acrylates/Ammonium Methacrylate copolymer may be in an amount of about 0.1 to about 3 wt. % based on the total weight of the cosmetic composition. In some instance, the amount of Styrene/Acrylates/Ammonium Methacrylate copolymer is, however, from about 0.5 to about 3 wt. %, about 1 to 3 wt. %, about 1.5 to about 3 wt. %, about 0.5 to about 2.5 wt. %, about 0.5 to about 2 wt. %.

Combination of Polyester-5 and Styrene/Acrylates/Ammonium Methacrylate Copolymer An unexpected water resistance effect as well as an improvement in the texture has been discovered arising from the combination of Polyester-5 and Styrene/Acrylates/ammonium Methacrylate copolymer. The synergistic effect may be achieved when a ratio of each of the film formers is within a suitable range.

The ratio of Polyester-5 and Styrene/Acrylates/ammonium Methacrylate copolymer may be any suitable ratio, including, but not limited to, a ratio between about 10:1 to about 1:5, alternatively between about 5:1 to about 1:3, alternatively between about 2:1 to about 1:1.

Cosmetic Composition

The compositions according to the instant disclosure may be prepared according to techniques that are well known to those skilled in the art, in particular those intended for the preparation of emulsions of oil-in-water or water-in-oil type. They may be in particular in the form of a simple or complex emulsion (O/W, W/O, O/W/O or W/O/W emulsion) such as a cream or a milk, in the form of a gel or a cream-gel, or in the form of a lotion.

Oils/Emollients

Examples of oils/emollients that may be included in the cosmetic compositions include: hydrocarbon-based oils of plant origin, such as liquid triglycerides of fatty acids containing from 4 to 10 carbon atoms, for instance heptanoic or octanoic acid triglycerides, or alternatively, for example, sunflower oil, corn oil, soybean oil, marrow oil, grapeseed oil, sesameseed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and caprylyl glycol; synthetic esters and ethers, especially of fatty acids, for instance Purcellin oil, 2-octyldodecyl stearate, 2-octyldodecyl erucate, isostearyl isostearate; hydroxylated esters, for instance isostearyl lactate, octyl hydroxystearate, octyldodecyl hydroxystearate, diisostearyl malate or triisocetyl citrate, tributyl citrate (in fla 888561 11); fatty alcohol heptanoates, octanoates or decanoates; polyol esters, for instance propylene glycol dioctanoate, neopentyl glycol diheptanoate and diethylene glycol diisononanoate; and pentaerythritol esters, for instance pentaerythrityl tetraisostearate, or isopropyl lauroyl sarcosinate, sold especially under the trade name Eldew SL 205 by the company Ajinomoto; linear or branched hydrocarbons, of mineral or synthetic origin, such as volatile or non-volatile liquid paraffins, and derivatives thereof, petroleum jelly, polydecenes, isohexadecane, isododecane, hydrogenated polyisobutene such as Parleam oil, or the mixture of n-undecane (Cn) and of n-tridecane (C13) sold under the reference Cetiol UT by the company Cognis; fluoro oils that are partially hydrocarbon-based and/or silicone-based, for instance those described in document JP-A-2 295 912; silicone oils, for instance volatile or non-volatile polymethylsiloxanes (PDMS) with a linear or cyclic silicone chain, which are liquid or pasty at room temperature, in particular volatile silicone oils, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; mixtures thereof.

Additional examples include benzoic acid esters of C9-C15 alcohols, isononyl iso-nonanoate, C12-C15 alkyl benzoate, or any combinations thereof.

Specific examples of oils/emollients include cocoglyceride, cyclomethicone, dimethicone, dicapryl maleate, caprylic/capric triglyceride, isopropyl myristate, octyl stearate, isostearyl linoleate, lanolin oil, coconut oil, cocoa butter, olive oil, avocado oil, aloe extracts, jojoba oil, castor oil, fatty acid, oleic acid, stearic acid, fatty alcohol, cetyl alcohol, hexadecyl alcohol, diisopropyl adipate, hydroxybenzoate esters, benzoic acid esters of C9-C15 alcohols, isononyl iso-nonanoate, alkanes, mineral oil, silicone, dimethyl polysiloxane, ether, polyoxypropylene butyl ether, polyoxypropylene cetyl ether, Ci2-Ci5 alkyl benzoate, aryl alkyl benzoate, Isopropyl Lauroyl sarcosinate, and any combinations thereof.

Examples of hydrophilic organic solvents that may be included in the sunscreen compositions include: monohydric C1-C8 alcohols such as ethanol, propanol, butanol, isopropanol, isobutanol; Polyethylene glycols from 6 to 80 ethylene oxides such as propylene glycol, isoprene glycol, butylene glycol, glycerol, sorbitol; mono or di-alkyl isosorbides such as dimethyl isosorbide.

Examples of amphiphilic organic solvents include: polypropylene glycol (PPG) like propylene glycol alkyl ester or alkyl ether of PPG like PPG-23 oleyl ether and PPG-36 oleate.

The above lists are only examples and not limiting.

The total amount of oils/emollient present in the compositions is typically about 0.1, 0.5, 1.0, or 2.5 wt. % to about 5.0, 7.5, 10.0, 15.0, 20.0, or 30 wt. % of the total weight of the composition.

Emulsifiers

The cosmetic compositions typically include at least one emulsifier such as an amphoteric, anionic, cationic or nonionic emulsifier, used alone or as a mixture, and optionally a co-emulsifier. The emulsifiers are chosen in an appropriate manner according to the emulsion to be obtained (W/O or O/W). The emulsifier and the co-emulsifier are generally present in the composition in a proportion ranging from 0.3% to 30% by weight and preferably from 0.5% to 20% by weight relative to the total weight of the composition.

For W/O emulsions, examples of emulsifiers that may be mentioned include dimethicone copolyols, such as the mixture of cyclomethicone and dimethicone copolyol sold under the trade name DC 5225 C by the company Dow Corning, and alkyl dimethicone copolyols such as the lauryl dimethicone copolyol sold under the name Dow Corning 5200 Formulation Aid by the company Dow Corning, and the cetyl dimethicone copolyol sold under the name Abil EM90™ by the company Goldschmidt. A crosslinked elastomeric solid organopolysiloxane comprising at least one oxyalkylene group, such as those obtained according to the procedure of Examples 3, 4 and 8 of U.S. Pat. No. 5,412,004 and of the examples of U.S. Pat. No. 5,811,487, especially the product of Example 3 (synthesis example) of U.S. Pat. No. 5,412,004, such as the product sold under the reference KSG 21 by the company Shin-Etsu, may also be used as surfactants for W/O emulsions.

For O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters; oxyalkylenated (oxyethylenated and/or oxypropylenated) fatty alcohol ethers; sugar esters such as sucrose stearate; and mixtures thereof.

The fatty acid esters of a sugar that can be used as nonionic amphiphilic lipids can be chosen in particular from the group comprising esters or mixtures of esters of a $C_8$-$C_{22}$ fatty acid and of sucrose, of maltose, of glucose or of fructose, and esters or mixtures of esters of a $C_{14}$-$C_{22}$ fatty acid and of methylglucose. The $C_8$-$C_{22}$ or $C_{14}$-$C_{22}$ fatty acids forming the fatty unit of the esters that can be used in the emulsion comprise a saturated or unsaturated linear alkyl chain having, respectively, from 8 to 22 or from 14 to 22 carbon atoms. The fatty unit of the esters can be chosen in particular from stearates, behenates, arachidonates, palmitates, myristates, laurates, caprates and mixtures thereof.

By way of example of esters or of mixtures of esters of a fatty acid and of sucrose, of maltose, of glucose or of fructose, mention may be made of sucrose monostearte, sucrose distearate, sucrose tristearate and mixtures thereof, such as the products sold by the company Croda under the name Crodesta F50, F70, F110 and F160 having, respectively, an HLB (Hydrophilic Lipophilic Balance) of 5, 7, 11 and 16; and, by way of example of esters or of mixtures of esters of a fatty acid and of methylglucose, mention may be made of the disearate of methylglucose and of polyglycerol-3, sold by the company Goldschmidt under the name Tegocare 450. Mention may also be made of glucose monoesters or maltose monoesters, such as methyl O-hexadecanoyl-6-D-glucoside and O-hexadecanoyl-6-D-maltoside.

The fatty alcohol ethers of a sugar that can be used as nonionic amphiphilic lipids can be chosen in particular form the group comprising ethers or mixtures of ethers of a $C_8$-$C_{22}$ fatty alcohol and of glucose, of maltose, of sucrose or of fructose, and ethers or mixtures of ethers of a $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers that can be used in the emulsion of the instant disclosure comprise a saturated or unsaturated linear alkyl chain having, respectively, from 8 to 22 or from 14 to 22 carbon atoms. The fatty unit of the ethers can be chosen in particular from decyl, cetyl, behenyl, arachidyl, stearyl, palmityl, myristyl, lauryl, capryl and hexadecanoyl units, and mixtures thereof such as cetearyl.

By way of example of fatty alcohol ethers of a sugar, mention may be made of alkylpolyglucosides, such as decylglucoside and laurylglucoside sold, for example, by the company Henkel under the respective names Plantaren 2000 and Plantaren 1200, cetostearylglucoside, optionally as a mixture with cetostearyl alcohol, sold, for example, under the name Montanov 68 by the company Seppic, under the name Tego-care CG90 by the company Goldschmidt and under the name Emulgade KE3302 by the company Henkel, and also arachidylglucoside, for example in the form of the mixture of arachidyl and behenyl alcohols and of arachidylglucoside sold under the name Montanov 202 by the company Seppic.

Use is more particularly made, as nonionic amphiphilic lipid of this type, of sucrose monostearate, sucrose distearate, sucrose tristearate and mixtures thereof, the distearate of methylglucose and of polyglycerol-3, and alkylpolyglucosides.

The glycerol fatty esters that can be used as nonionic amphiphilic lipids can be chosen in particular from the group comprising the esters formed from at least one acid comprising a saturated linear alkyl chain having from 16 to 22 carbon atoms, and from 1 to 10 glycerol units. Use may be made of one or more of these glycerol fatty esters in the emulsion of the instant disclosure.

These esters may be chosen in particular from stearates, behenates, arachidates, palmitates and mixtures thereof. Stearates and palmitates are preferably used.

By way of example of a surfactant that can be used in the emulsion of the instant disclosure, mention may be made of decaglycerol monostearate, distearate, tristearate and pentastearate (10 glycerol units) (CTFA names: polyglyceryl-10 stearate, polyglyceryl-10 distearate, polyglyceryl-10 tristearate, polyglyceryl-10 pentastearate), such as the products sold under the respective names Nikkol Decaglyn 1-S, 2-S, 3-S and 5-S by the company Nikko, and diglyceryl monostearate (CTFA name: polyglyceryl-2 stearate) such as the product sold by the company Nikko under the name Nikkol DGMS.

The sorbitan fatty esters that can be used as nonionic amphiphilic lipids chosen in particular from the group comprising esters of a $C_{16}$-$C_{22}$ fatty acid and of sorbitan and oxyethylenated esters of a $C_{16}$-$C_{22}$ fatty acid and of sorbitan. They are formed from at least one fatty acid comprising at least one saturated linear alkyl chain, having, respectively, from 16 to 22 carbon atoms, and from sorbitol or from ethoxylated sorbitol. The oxyethylenated esters generally comprise from 1 to 100 ethylene oxide units, and preferably from 2 to 40 ethylene oxide (EO) units.

These esters can be chosen in particular from stearates, behenates, arachidates, palmitates and mixtures thereof. Stearates and palmitates are preferably used.

By way of example of sorbitan fatty ester and of an oxyethylenated sorbitan fatty ester, mention may be made of sorbitan monostearate (CTFA name: sorbitan stearate) sold by the company ICI under the name Span 60, sorbitan monopalmitate (CTFA name: sorbitan palmitate) sold by the company ICI under the name Span 40, or sorbitan 20 EO tristearate (CTFA name: polysorbate 65) sold by the company ICI under the name Tween 65.

The ethoxylated fatty ethers are typically ethers made up of 1 to 100 ethylene oxide units and of at least one fatty alcohol chain having from 16 to 22 carbon atoms. The fatty chain of the ethers can be chosen in particular from behenyl, arachidyl, stearyl and cetyl units, and mixtures thereof, such as cetearyl. By way of example of ethoxylated fatty ethers, mention may be made of ethers of behenyl alcohol comprising 5, 10, 20 and 30 ethylene oxide units (CTFA names: beheneth-5, beheneth-10, beheneth-20 and beheneth-30), such as the products sold under the names Nikkol BBS, BB10, BB20 and BB30 by the company Nikko, and the ether of stearyl alcohol comprising 2 ethylene oxide units (CTFA name: steareth-2), such as the product sold under the name Brij 72 by the company ICI.

The ethoxylated fatty esters that can be used as nonionic amphiphilic lipids are esters made up of 1 to 100 ethylene oxide units and of at least one fatty acid chain comprising from 16 to 22 carbon atoms. The fatty chain of the esters can be chosen in particular from stearate, behenate, arachidate and palmitate units, and mixtures thereof. By way of example of ethoxylated fatty esters, mention may be made of the ester of stearic acid comprising 40 ethylene oxide units, such as the product sold under the name Myrj 52 (CTFA name: PEG-40 stearate) by the company ICI, and the ester of behenic acid comprising 8 ethylene oxide units (CTFA name: PEG-8 behenate), such as the product sold under the name Compritol HD5 ATO by the company Gattefosse.

The block copolymers of ethylene oxide and of propylene oxide that can be used as nonionic amphiphilic can be chosen in particular from poloxamers and in particular from Poloxamer 231, such as the product sold by the company ICI under the name Pluronic L81 of formula (V) with x=z=6, y=39 (HLB 2); Poloxamer 282, such as the product sold by the company ICI under the name Pluronic L92 of formula (V) with x=z=10, y=47 (HLB 6); and Poloxamer 124, such as the product sold by the company ICI under the name Pluronic L44 of formula (V) with x=z=11, y=21 (HLB 16).

As nonionic amphiphilic lipids, mention may also be made of the mixtures of nonionic surfactants described in document EP-A-705593, incorporated herein for reference.

Suitable hydrophobically-modified emulsifiers include, for example, inulin lauryl carbamate, commercially available from Beneo Orafti under the tradename Inutec SP1.

The above lists are only examples and not limiting.

The total amount of emulsifier present in the compositions is typically in an amount of about 0.1, 0.2, or 0.5 wt. % to about 4.0, 5.0, 6.0, or 7.5 wt. %, based on the total weight of the composition.

Gelling Agent

Gelling agents may also be included in the sunscreen compositions. Examples of suitable hydrophilic gelling agents include carboxyvinyl polymers such as the Carbopol products (carbomers) and the Pemulen products (acrylate/C10-C30-alkylacrylate copolymer); polyacrylamides, for instance the crosslinked copolymers sold under the names Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, which are optionally crosslinked and/or neutralized, for instance the poly(2-acrylamido-2-methylpropanesulfonic acid) (CTFA name\ammonium polyacryldimethyltauramide); cellulose-based derivatives such as hydroxyethylcellulose; polysaccharides and especially gums such as xanthan gum; and mixtures thereof.

Lipophilic gelling agents (thickeners) that may be mentioned include modified clays such as hectorite and its derivatives, for instance the products sold under the name bentone.

In some instances, the gelling agent is ammonium acryloyldimethyltaurate/steareth-25 methacrylate crosspolymer, commercially available from Clariant under the tradename Aristoflex HMS.

The above lists are only examples and not limiting.

The gelling agent is typically used in an amount of about 0.05 to about 1.5% by weight, from about 0.08 to about 1.0% by weight, or about 0.1 to about 0.5% by weight, based on the total weight of the composition.

Plasticizer

Plasticizers may be included to influence the film formation properties of the sulfopolyester and which may influence delivery rate of ultraviolet absorbers to the skin. These plasticizers include but are not limited to ingredients such as propylene glycol, glycerin, methyl pentane diol, butylene glycol, hexylene glycol, octanediol, phenoxyethanol, cyclohexane dimethanol, glycolic acid, lactic acid, acetic acid, propionic acid, salicylic acid, triethyl citrate, acetoxy triethyl citrate, tributyl citrate, triacetin, glycerol esters of acetic, propionic acid and the like, and mixtures thereof.

The instant disclosure will be better understood from the examples that follow, all of which are intended for illustrative purposes only and are not meant to limit the scope of the instant disclosure in any way.

More exhaustive but non-limiting lists of components useful in the compositions disclosed herein are presented below.

Example 1

A cosmetic composition containing the combination of the Polyester-5 and the Syntran® latex 5620 CG was prepared. The components of the composition are presented in Table 1, below.

TABLE 1

| Phase | Chemical Name | % wt/wt |
|---|---|---|
| A | SILICONE | 4-10 |
| A | SUN FILTER (s) | 10-30 |
| A | SURFACTANT | 0.1-6 |
| A | ISOHEXADECANE | 2-8 |
| A | PRESERVATIVE | 0.02-1.8 |
| B | WATER | 20-30 |
| B | POLYESTER-5 | 0.5-4 |
| B | CHELATING AGENT | 0.05-0.2 |
| C | WATER | QS |
| D | PLASTICIZER | 0.01-0.15 |
| D | STYRENE/ACRYLATES/AMMONIUM METHACRYLATE COPOLYMER | 0.1-3 |

The composition above was prepared by first dissolving the components of phase A together at 75-80° C. The components of phase B were mixed at 75-80° C. separately. The mixture B was added to A quickly and homogenized for 20 minutes. The solution obtained was then started to cool to room temperature. While cooling, add phase C, and homogenize for 15 min. Premix phase D and add below 40° C., and homogenize for 3 minutes. Then cool down to 25° C.

Example 2

Water-Resistance Properties

The compositions in the tables below were prepared as described previously in the Example 1, but with different quantity and type of film formers. The water resistance was measured.

TABLE 2

Inventive examples

| Properties | Film Formers | INV EX1 | INV EX2 | INV EX3 | INV EX4 |
|---|---|---|---|---|---|
| | Syntran® 5620 CG, % | 0.82 | — | 2.82 | 2 |
| | Syntran® 5760 CG, % | — | 0.82 | — | — |
| | AQ™38S, % | 2 | 2 | — | — |
| | Baycusan C1004, % | — | — | — | — |
| | Epitex 66, % | — | — | — | — |
| In VITRO (WR*), % | | 46 | 46 | 61 | 68 |
| In VIVO (WR), % | | 95 | 92 | 95 | N/A |

*WR = Water Resistance

TABLE 3

Comparative examples

| | COMP EX1 | COMP EX2 | COMP EX 3 | COMP EX 4 | COMP EX 5 |
|---|---|---|---|---|---|
| Film Formers | | | | | |
| Syntran® 5620 CG, % | — | — | — | — | — |
| Syntran® 5760 CG % | — | — | — | — | — |
| AQ™38S, % | — | 2 | 2.82 | — | 2 |
| Baycusan® C1004, % | — | — | — | 0.82 | — |
| Epitex 66% | — | — | — | — | 0.9 |
| Properties | | | | | |
| In VITRO (WR*), % | 29 | 17 | 18 | 41 | N/A |
| In VIVO (WR), % | N/A | 23 | N/A | 25 | 97 |

In Table 2, the Water Resistance properties of inventive examples containing different types of film formers are shown. The Water Resistance properties of the compositions increase when certain types of film formers are combined.

In Table 3, the Water Resistance properties of comparative examples containing different types of film formers or none (see Comparative example 1) are shown. Depending on the polymer combinations, the Water Resistance properties are not the same. The Water Resistance properties were measured in vivo and in vitro. The in vivo method is the FDA approved method.

The control example (Comparative example 1 from Table 3), containing none of the film formers that were being studied, exhibited an average or low Water Resistance properties (29% in Vitro) compared to the inventive and comparative examples. In Table 1, the association between Syntran® 5620 CG and AQ™38S and the association between Syntran® 5760 CG and AQ™38S exhibited the same high Water Resistance properties (46% in Vitro and 95% in Vivo in the former, 46% in Vitro and 92% in Vivo in the later).

In the inventive example 3, only the Syntran® 5620 CG was present at the same concentration as the combination between the two previous film formers. The Water Resistance results were better for the in Vitro results compared to the inventive examples 1 and 2 (61% instead of 46%), and the in Vivo results were close compared to the inventive examples 1 and 2 (95% instead of 92 and 95%, respectively).

In the inventive example 4 and the comparative example 2, the concentrations studied for each of the active ingredients was 2% instead of 2.82%, but it did show that the Water Resistance properties were different when the two film formers were used separately. In the inventive example 4 comprising Syntran® 5620 CG, the in Vitro Water Resistance measured was 68%. In the comparative example 2 comprising AQ™38S, the in Vitro Water Resistance measured was 17%. These results confirmed that there is a synergy of the Water Resistance when the two film formers are combined.

The comparative data from Table 2 confirmed the synergy observed between Syntran® 5620 CG and AQ™38S. It did also show that the synergy did not work with any type of film former. For example, in the comparative example 4, even though two film formers were combined at the same concentration than the inventive examples, if a different film former such as Baycusan® C1004 was used, the in Vitro and in Vivo water resistance properties were not as good as the ones using Syntran® 5620 CG in combination with AQ™38S.

Example 3

Stickiness

The following table is showing the stickiness properties of the inventive and comparatives examples.

TABLE 4

| | | Stickiness | in vivo WR* | in vitro WR* |
|---|---|---|---|---|
| INV EX 3 | Syntran ® 5620 CG | ++ | 95% | 61% |
| INV EX 1 | Syntran ® 5620 CG + AQ ™38S | − | 95% | 46% |
| INV EX 2 | Syntran ® 5760 CG + AQ ™38S | + | 92% | 46% |
| COMP EX 1 (control) | no film former | − | — | 29% |
| COMP EX 4 | Baycusan ® C1004C + AQ ™38S | ++++ | 25% | 41% |
| COMP EX 5 | Epitex 66 + AQ ™38S | +++++ | 97% | — |

Legend:
(+) stickiness level;
(−) no stickiness
*WR = Water Resistance

In order to measure the in vivo sensation on the skin, the formulation was applied to the arm and the stickiness was attributed.

In Table 4, three inventive examples are shown in comparison to comparative examples in order to illustrate the stickiness levels of the products. The inventive examples demonstrate an increase in the Water Resistance properties clearly showing the unexpected synergy between the two film formers, in particular, inventive example 1. Furthermore, the inventive example 1 is the one showing the best feeling on the skin compared to inventive examples 2 and 3. It appears though that the combination between Syntran® 5620 CG and AQ™38S is the best combination for the overall properties (Water Resistance-and stickiness).

Other than in the operating examples and unless otherwise stated, all numbers expressing quantities of ingredients and/or reaction conditions are to be understood as being modified in all instances by the term "about".

As used herein, the terms "comprising," "having," and "including" are used in their open, non-limiting sense.

The terms "a," "an," and "the" are understood to encompass the plural as well as the singular.

The expression "at least one" means "one or more" and vice versa, and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic composition comprising:
   (a) Sulfopolyester;
   (b) Styrene/Acrylates/Ammonium Methacrylate copolymer;
   wherein the combination of Sulfopolyester and Styrene/Acrylates/Ammonium Methacrylate copolymer improves the water resistance of the cosmetic composition and provides a non-sticky cosmetic composition.

2. The composition of claim 1, wherein the Sulfopolyester of (a) includes polyester-5.

3. The composition of claim 2, wherein the polyester of (a) consists of polyester-5.

4. The composition of claim 1, wherein (a) is from about 0.5 to about 4 wt. % based on the total weight of the cosmetic composition.

5. The composition of claim 1, wherein (a) is from about 1 to about 3.5 wt. % based on the total weight of the cosmetic composition.

6. The composition of claim 1, wherein (a) is from about 1.5 to about 3 wt. % based on the total weight of the cosmetic composition.

7. The composition of claim 1, wherein (b) is from about 0.1 to about 3 wt. % based on the total weight of the cosmetic composition.

8. The composition of claim 1, wherein (b) is from about 0.2 to about 2.5 wt. % based on the total weight of the cosmetic composition.

9. The composition of claim 1, wherein (b) is from about 0.5 to about 2 wt. % based on the total weight of the cosmetic composition.

10. The composition of claim 1, including a ratio of the polymer of (a) to the polymer of (b) is between about 10:1 to about 1:5.

11. The composition of claim 1, including a ratio of the polymer of (a) to the polymer of (b) is between about 5:1 to about 1:3.

12. The composition of claim 1, wherein the ratio of the polymer of (a) to the polymer of (b) is between about 2:1 to about 1:1.

13. The composition of claim 1, wherein the cosmetic composition is a skin care composition.

14. The composition of claim 1, wherein the cosmetic composition is a make-up composition.

* * * * *